United States Patent [19]

Niwa et al.

[11] 4,220,517
[45] Sep. 2, 1980

[54] OXYGEN CONCENTRATION SENSING APPARATUS

[75] Inventors: Hitoshi Niwa, Anjo; Naoto Miwa, Tsushima; Masatoshi Suzuki, Kariya; Masami Ouki, Nagoya, all of Japan

[73] Assignee: Nippondenso Co., Ltd., Kariya, Japan

[21] Appl. No.: 24,773

[22] Filed: Mar. 28, 1979

[30] Foreign Application Priority Data

May 16, 1978 [JP] Japan ................... 53-58105

[51] Int. Cl.$^2$ ........................................... G01N 27/58
[52] U.S. Cl. ................................................ 204/195 S
[58] Field of Search ..................... 204/195 S, 1 S; 123/119 E, 119 EC; 60/276; 422/98; 324/29

[56] References Cited

U.S. PATENT DOCUMENTS

| | | | |
|---|---|---|---|
| 2,782,103 | 2/1957 | Prentiss | 60/276 X |
| 3,940,327 | 2/1976 | Wagner et al. | 204/195 S |
| 4,107,019 | 8/1978 | Takao et al. | 204/195 S |
| 4,130,797 | 12/1978 | Hattori et al. | 422/98 X |

FOREIGN PATENT DOCUMENTS 2304075 8/1974 Fed. Rep. of Germany ....... 204/195 S
52-26284 2/1977 Japan .

*Primary Examiner*—G. L. Kaplan
*Attorney, Agent, or Firm*—Cushman, Darby & Cushman

[57] ABSTRACT

In an oxygen concentration sensing apparatus comprising a solid, oxygen ion conductive, electrolyte and intervening between two electrodes to generate across the two electrodes a potential difference due to a difference in oxygen concentrations at the boundaries between the two electrodes and the solid electrolyte, one of the two electrodes is made of a metal performing catalytic action, one end portion of the one electrode is embedded in the solid electrolyte to be fixed thereby, the other end portion of the one electrode projects outwardly of the solid electrolyte, a portion of the one electrode contacting with an outer surface of the solid electrolyte is hermetically sealed with a nonconductive layer of a heat-resistant material, and the other electrode is made of a porous metal performing catalytic action and is disposed on the outer surface of the solid electrolyte but preventing the other electrode from being in contact with the one electrode.

Further, the oxygen concentration sensing apparatus may be provided with an electric circuit for making an electric current flow intermittently from the one electrode through the solid electrolyte to the other electrode thereby to maintain the oxygen concentration at the boundary between the one electrode and the solid electrolyte at a constant level.

9 Claims, 11 Drawing Figures

OXYGEN CONCENTRATION SENSING APPARATUS

BACKGROUND OF THE INVENTION

1. Field of the Invention

This invention relates to oxygen concentration sensing apparatus conveniently available for sensing the oxygen concentration of exhaust gas from internal combustion engines for automobiles, as an example of its application.

2. Description of the Prior Art

Conventional oxygen concentration sensing apparatus of this kind as disclosed in Japanese patent application Kokai (Laid-Open) No. 52-119989, has two electrodes. One of the electrodes is made of a porous metal performing catalytic action and is exposed to the exhaust gas to be tested. The other one of the two electrodes is made of the same metal as that of the first and is embedded in a solid, oxygen ion conductive, electrolyte so as to prevent its exposure to the exhaust gas. However, in such apparatus, a lead wire is joined to the electrode embedded in the solid electrolyte, and hence, in the process of actual fabrication of the apparatus, an electrode and a lead wire are joined together before the application of the electrolyte by welding, and the joined assembly is placed in the solid electrolyte, e.g., $ZrO_2$-$Y_2O_3$, and is molded. Finally the molded assembly is sintered. The sintering temperature in this case reaches about 1500° to 1700° C., since it is necessary to make $ZrO_2$ and $Y_2O_3$ react in the state of a solid solution to obtain a stable composition. While a platinum electrode is fusion-proof property and oxidization-proof under such temperatures, a lead wire is made of gold, nickel, chrome or stainless steel presents a problem in that is may use and/or oxidize. Therefore, it is not possible to use such materials for making the lead wire, and hence a catalyzing metal of the platinum family must be used as the lead wire material. While one of the electrodes is embedded in the solid electrolyte to suppress its catalytic action, the lead wire made of a catalyzing metal of the platinum family and joined thereto effects catalytic action. Therefore, if the entire electrolyte assembly is exposed to the exhaust gas to be tested, and the external bare portions of the two lead wires, which are in contact with an outer surface of the solid electrolyte, are placed in the exhaust gas to be tested, no potential difference appears between the two electrodes. Thus, it has been found impossible to obtain any output electromotive force with this conventional structure.

Accordingly, in the conventional oxygen concentration sensing apparatus it becomes necessary to have the lead wire joined to the electrode embedded in the solid electrolyte exposed to the atmosphere in order to have an electromotive force generated by a difference in oxygen concentrations. Hence the solid electrolyte should have a tubular shape with one end thereof being open and the other end thereof being closed, thus having a U-shaped longitudinal section. Such a construction still has the same drawbacks as well-known conventional oxygen concentration sensing apparatus. The lack of an effective barrier between the exhaust gas and the atmosphere and of thermal-shock-proof construction as well as a thermal response characteristic of the solid electrolyte used, causes these same drawbacks.

SUMMARY OF THE INVENTION

It is, therefore, the object of this invention in view of the abovementioned problems to provide an oxygen concentration sensing apparatus wherein a lead wire connected to a catalyzing electrode embedded in a solid electrolyte is made of the same catalyzing metal as that of the embedded electrode and is incorporated with the electrode. A portion of the electrode, incorporated with the lead wire, which contacts an outer surface of the solid electrolyte, is hermetically sealed with a nonconductive layer of a heat-resistant material to prevent the portion from contacting an inflammable gas even when the solid electrolyte assembly is exposed to the gas. A potential difference is generated between the abovementioned electrode and an exposed porous electrode made of a catalyzing metal due to a difference in oxygen concentrations between the two portions of the solid electrolyte which are in contact with the two electrodes, respectively. Thus, it becomes possible to expose the complete solid electrolyte assembly to an inflammable gas with a simple construction because of the complete elimination of the necessity of maintaining gastightness between the inflammable gas and the atmosphere, which is taken as a reference standard of an oxygen gas source. Accordingly, the solid electrolyte may be cylindrical, and flat or the like, and of small size. The present invention is particularly advantageous with respect to a thermal-shock-proof property and a thermal response characteristic.

According to this invention one of the electrodes of the oxygen concentration sensing apparatus is made of a metal performing catalytic action, an end portion of which electrode is embedded in a solid electrolyte to be fixed thereby and a portion of which electrode contacting with an outer surface of the solid electrolyte is hermetically sealed with a nonconductive layer of a heat-resistant material. The other electrode is made of a porous metal performing catalytic action and is disposed on the outer surface of the solid electrolyte, not contacting the other electrode. With the abovementioned construction, even if all the solid electrolyte assembly is exposed to an inflammable gas, no inflammable gas touches the portion of the embedded electrode contacting with the outer surface of the solid electrolyte due to the hermetic sealing by the layer of the heat-resistant material. Thus, the potential difference between the two electrodes caused by a difference in oxygen concentrations does not become null because inflammable gas touches the abovementioned portion, as experienced in conventional apparatus. Since exposure of the entire solid electrolyte assembly to an inflammable gas is possible, now there is no necessity to expose a portion of the solid electrolyte to the atmosphere which is taken as a reference standard of an oxygen gas source, as done in conventional apparatus, and therefore it becomes entirely unnecessary to maintain a gas tight barrier between the atmosphere and the gas, which allows a quite simple construction.

Since it becomes completely unnecessary to maintain gastightness between the atmosphere and the inflammable gas, as done in conventional apparatus, it is no longer necessary that the solid electrolyte have a complex shape and large external size so that gastightness can be maintained. Further, since the entire solid electrolyte assembly can be exposed to the inflammable gas, little localized variations or differentials of temperature occur across the solid electrolyte, which brings such advantages as improving the thermal-shockproof property as well as the thermal response characteristic of the solid electrolyte thereby allowing it to promptly reach an operating temperature.

Further, beside the abovedescribed featured construction of the oxygen concentration sensing apparatus according to this invention, it is possible to add to the abovedescribed construction an electric circuit for making an electric current flow intermittently from the embedded electrode to the electrode on the outer surface of the solid electrolyte. As a result of such an electric circuit, when oxygen ions move from the embedded electrode to the electrode on the outer surface of the solid electrolyte, reducing the oxygen concentration in the region around the embedded electrode to thereby lower the output level across both electrodes, it is possible to supply residual oxygen in the inflammable gas to the region around the embedded electrode by feeding an electric current from the electric circuit, thereby recovering the output level across both electrodes from a reduced level to a normal output level. Accordingly, there can be brought a remarkable advantage that the concentration of residual oxygen in an inflammable gas can be sensed accurately by maintaining the oxygen concentration in the region around the embedded electrode at a constant level by the intermittent flow of the electric current.

DESCRIPTION OF THE PREFERRED EMBODIMENTS

Figure 1:
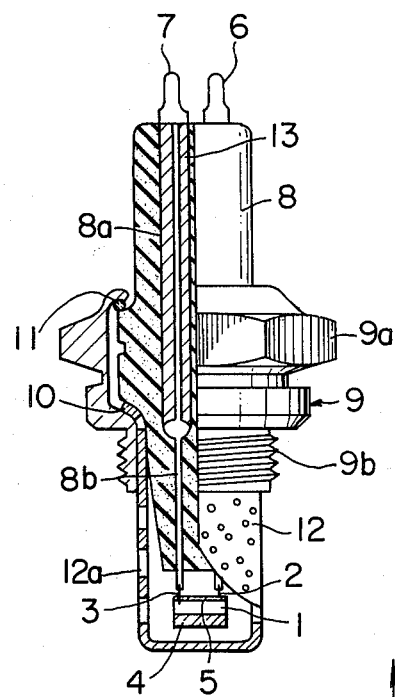
FIG. 1 is a local sectional drawing showing the complete construction of the apparatus of a first embodiment of this invention.
Figure 2:
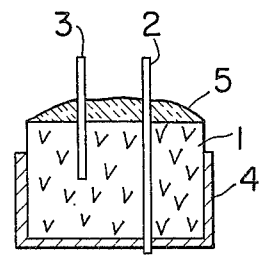
FIG. 2 is a sectional drawing showing a main part of the apparatus shown in FIG. 1.

The present invention will be described hereunder with respect to the embodiments thereof shown in the accompanying drawings. In FIGS. 1 and 2, numeral 1 designates a solid conductive oxygen ion electrolyte having a shape of a rectangular parallelepiped which is obtained by sintering a mixture of suitable amounts of $ZrO_2$ and $Y_2O_3$ at a high temperature (about 1500° to 1700° C.) to form a solid solution. Numeral 2 designates a lead wire made of platinum which extends from the interior of the solid electrolyte. One or both ends of lead wire 2 penetrate an outer surface of the solid electrolyte to project therefrom. Numeral 3 designates an electrode made of platinum an end of which is embedded and firmly fixed in the solid electrolyte 1. The electrolyte material is pressed and molded into a rectangular parallelepiped shape and thereafter it is subjected to a sintering process, thus fixing the lead wire 2 and the electrode 3 in the solid electrolyte 1 due to the shrinking action occurring in the sintering process. Numeral 4 designates a conductive porous thin layer electrode made of platinum disposed on five outer surfaces of the solid electrolyte 1, which is electrically connected to the projecting end of the lead wire 2. The electrode 4 is formed, for example by a chemical plating process. Numeral 5 designates a layer made of a heat-resistant material, having a high density which is obtained by melting a heat-resistant glass-like coating material onto electrolyte. The heat-resistant material layer 5 is disposed to cover an outer surface the solid electrolyte 1 to hermetically seal the portions of the lead wire 2 and the electrode 3, which are in contact with the outer surface of the solid electrolyte 1, against an inflammable gas such as an exhaust gas from internal combustion engines for automobiles. Numerals 6 and 7 designate terminal rods made of nickel, for example. Each of the terminal rods 6 and 7 is inserted in penetrating holes 8a and 8b provided in a cylindrical insulator 8 made of high strength alumina porcelain having thermal resistivity and nonconductivity, and each of the terminal rods 6 and 7 is fixed gastightly at the portion of the penetrating hole 8a having a greater bore with a heat-resistant glass-like material 13 intervening between each of the terminal rods 6 and 7 and the inner wall of the penetrating hole 8a which material 13 has been solidified after melting. Further, the lead wire 2 and the electrode 3 of the solid electrolyte 1 are joined by welding with the terminal rods 6 and 7, respectively, so that electrical conduction is assured therebetween, respectively. Numeral 9 designates a cylindrical housing made of a metal having thermal resistivity and corrosion resistance. The insulator 8 is supported inside the housing 9 with a ring-shaped metallic packing 10 and a caulking ring 11 intervening therebetween. The insulator 8 and the housing 9 are fixed to each other by heating and caulking a portion of the housing 9 which is opposite to the caulking ring 11. The housing 9 is provided with a hexagon nut portion 9a and a threaded portion 9b. Numeral 12 designates a cylindrical protective cover provided with a number of perforations 12a and made of a heat-resistant and corrosion-proof metal. The protective cover 12 is fixed to the lower portion of the housing 9 by welding to serve as a cover for the solid electrolyte 1. The housing 9 is designated so as to be fixed onto an exhaust pipe (not shown) of internal combustion engines for automobiles through its threaded portion 9b allowing all the solid electrolyte 1 to be exposed to an exhaust gas passing through the exhaust pipe.

An explanation will be given hereinafter on the operation of the oxygen concentration sensing apparatus of this invention having the structure such as mentioned above.

Figure 3:
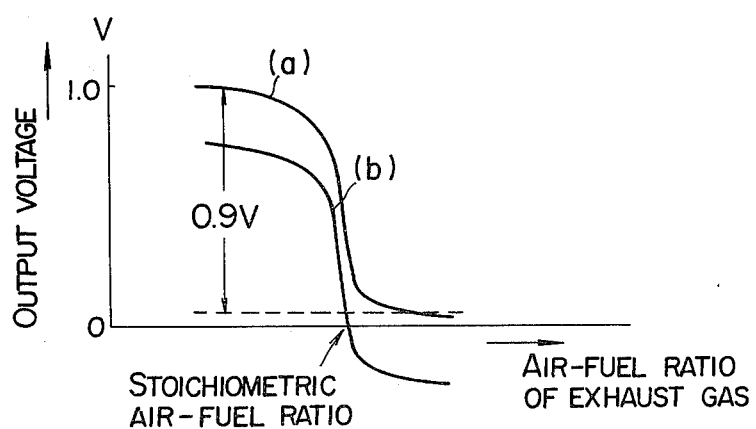
FIGS. 3 and 4 show characteristic curves for illustrating the operation of the apparatus of this invention.

When the concentration of residual oxygen in an exhaust gas is low, that is, when the air-fuel ratio of an exhaust gas is low, namely, when the air-fuel mixture is rich, the concentration of residual oxygen in the solid electrolyte 1 becomes richer than that in the exhaust gas at that time, so that the reaction represented by $O_2 + 4e^- \rightarrow 2O^{2-}$ progresses at the portion of the electrode 3 embedded in the solid electrolyte 1 and the above oxygen ion produces an oxygen gas according to the reaction represented by $2O^{2-} \rightarrow O_2 + 4e^-$ which occurs at the portion of the electrode 4, thereby causing a potential difference of about 1.0 V to appear between the electrodes 3 and 4. On the other hand, when the air-fuel ratio of an exhaust gas is high, namely, the concentration of residual oxygen in the exhaust gas is high, the transfer of oxygen ions from the electrode 3 to the electrode 4 decreases and the potential difference between the electrodes 3 and 4 is reduced to about 0.1 V. The relationship of the output voltage across the electrodes 3 and 4 versus the air-fuel ratio of an exhaust gas is shown in FIG. 3. As shown in FIG. 3, the characteristic curve (a) holds in an initial state, however, as time elapses, the concentration of residual oxygen at the boundary between the electrode 3 and the solid electrolyte 1 is reduced, so that the characteristic curve (b) appears after the lapse of about five minutes, thus showing a decreased output level lower than the initial output level. At this time, if an electric current is made to flow from the electrode 3 through the solid electrolyte 1 to the electrode 4, residual oxygen in an exhaust gas turns oxygen ions at the boundary between the electrode 4 and the solid electrolyte 1 according to the reaction represented by $O_2+4e^-\rightarrow 2O^{2-}$, and the oxygen ions move and turn an oxygen gas at the boundary between the electrode 3 and the solid electrolyte 1 according to the reaction represented by $2O^{2-}\rightarrow O_2+4e^-$, whereby an oxygen gas is supplied to the circumference of the electrode 3, thereby raising the decreased output level and causing the characteristic curve to be restored to the initial one indicated by (a).

Figure 4:
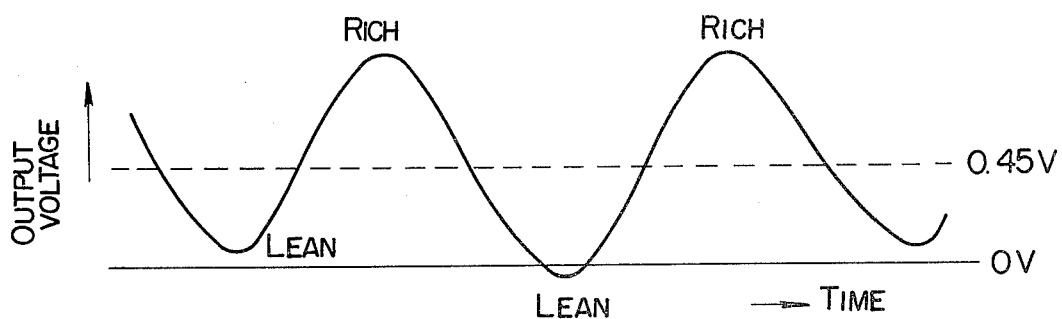

In the practical use of the oxygen concentration sensing apparatus of this invention, if the output level has become equal to or lower than zero volts when the air-fuel ratio of an exhaust gas is high, namely, when the air-fuel mixture is lean as shown in FIG. 4, an electric current is supplied to flow from the electrode 3 through the solid electrolyte 1 to the electrode 4 thereby to raise the output level.

Figure 5:
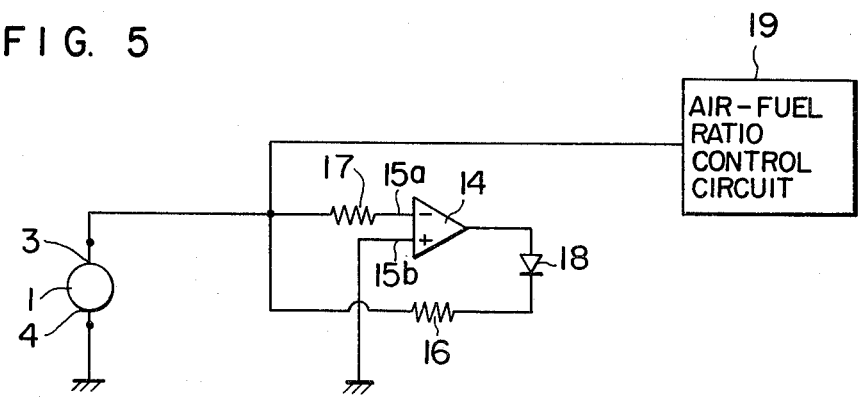
FIG. 5 shows an electric circuit for use in a second embodiment of this invention.
Figure 6:
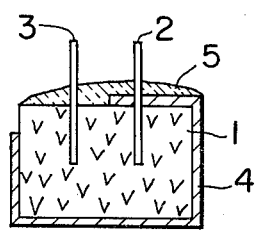
FIGS. 6 to 11 are sectional drawings showing various types of arrangement of electrodes in the apparatus of the first embodiment of this invention.
Figure 7:
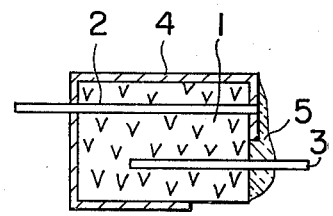
Figure 8:
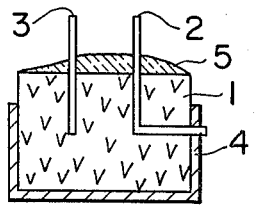
Figure 9:
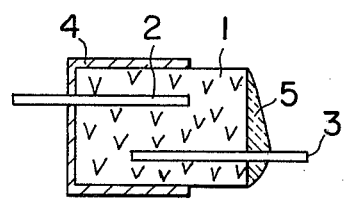
Figure 10:
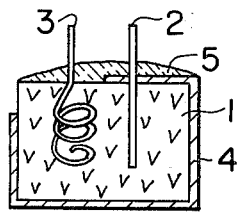
Figure 11:
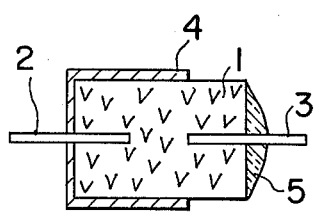

Next, an explanation will be given on the construction of a practical electric circuit. In FIG. 5, numeral 14 designates a comparator, 15a an inverted input terminal of the comparator 14, 15b a noninverted input terminal of the comparator 14 which is grounded. Numeral 16 designates a resistor whose resistance value is 2MΩ, for example. Numeral 17 designates a resistor which is connected to the side of the noninverted input terminal 15b and whose resistance value is 10KΩ, for example. Numeral 18 designates a reverse-current blocking diode. Here, the output voltage generated across the electrode 3 and the electrode 4, which is led to ground, of the solid electrolyte 1 is applied between the inverted input terminal 15a of the comparator 14 and ground, and the output voltage is applied also to an air-fuel ratio control circuit 19 as an input signal thereto. Further, the air-fuel ratio control circuit 19 may be one such as disclosed in Japanese patent application Kokoku (Post-Examination Publication) No. 52-26284, and is designed to control an air-fuel ratio with the abovedescribed output voltage which is supplied as an input signal to the comparator circuit.

The operation of the electric circuit of the abovementioned structure will be described hereunder. When the output voltage generated across the electrodes 3 and 4 of the solid electrolyte 1 becomes equal to or lower than zero volt, the comparator 14 produces an output voltage of 12 volts at its output terminal, which output voltage causes an electric current of 6 μA to flow through the diode 18, the resistor 16, the electrode 3, the solid electrolyte 1 and the electrode 4. Then, when the output voltage developed across the electrodes 3 and 4 exceeds zero volt, the output voltage of the comparator 14 becomes zero and the electric current from the electrode 3 to the electrode 4 stops flowing. Thereafter, when the output voltage across the electrodes 3 and 4 becomes again equal to or lower than zero volts, an electric current flows again from the electrode 3 to the electrode 4. As a result of the repeated interruption of the electric current flow, the concentration of oxygen at the boundary between the electrode 3 and the solid electrolyte 1 can be maintained constant.

FIGS. 6 to 11 show other types of the main part of the apparatus comprising the solid electrolyte, electrodes, lead wire and heat-resistant material layer.

Further, although the invention has been described with respect to the hereinabove described and illustrated embodiments, the invention is not restricted only to such embodiments, but may encompass various modifications such as shown below:

(1) The kind of materials for making the heat-resistant material layer 5 is not limited to heat-resistant glass, but the layer 5 may of course be made of a material such as alumina, zirconia, etc.

(2) The material for making the electrode 3, lead wire 2 and electrode 4 is not limited to platinum, but may include other metal elements such as rhodium and palladium and alloys such as platinum-rhodium and platinum-palladium.

(3) The material for making the solid electrolyte 1 is not limited to $Y_2O_3$-$ZrO_2$, but may include $CaO$-$ZrO_2$, etc. Besides, the solid electrolyte 1 may have a cubic, cylindrical or the like shape.

(4) The oxygen concentration sensing apparatus according to this invention is used only to detect the oxygen concentration in an exhaust gas from internal combustion engines for automobiles, but also may have other various fields of application.

(5) It is of course possible to have the lead wire 2 electrically connected to the housing 9.

We claim:

1. An oxygen concentration sensing apparatus comprising:
 a solid electrolyte having oxygen ion conductivity;
 a first electrode made of a metal performing catalytic action, said first electrode having a first portion embedded in said electrolyte and a second portion projecting outwardly from the outer surface of said electrolyte;
 a second electrode made of a porous metal performing catalytic action, disposed on the outer surface of said electrolyte and separated from said first electrode; and
 means for hermetically sealing the intersection of said first electrode and said electrolyte outer surface, said sealing means including a layer of nonconductive, heat-resistant material.

2. An oxygen concentration sensing apparatus comprising:
 a solid electrolyte having oxygen ion conductivity;
 a first electrode made of a metal performing catalytic action, said first electrode having a first portion embedded in said electrolyte and a second portion projecting outwardly from the outer surface of said electrolyte;
 a second electrode made of a porous metal performing catalytic action, disposed on the outer surface of said electrolyte and separated from said first electrode;
 a lead wire electrically connecting said second electrode, said lead wire projecting outwardly from the outer surface of said electrolyte; and
 means for hermetically sealing the intersection of said first electrode and said electrolyte outer surface, said sealing means including a layer of nonconductive, heat-resistant material.

3. An oxygen concentration sensing apparatus according to claim 2, wherein the end of said lead wire and said second portion of said first electrode, both projecting outwardly of said solid electrolyte, are connected to output terminals, respectively.

4. An oxygen concentration sensing apparatus according to claim 2, wherein the end of said leading wire projecting outwardly of said solid electrolyte is grounded, and said second portion of said first electrode projecting outwardly of said solid electrolyte is connected to an output terminal.

5. An oxygen concentration sensing apparatus according to claim 4, wherein said solid electrolyte has a rectangular parallelepiped, cubic or cylindrical shape.

6. An oxygen concentration sensing apparatus according to claim 2, wherein each of said first electrode, lead wire and second electrode is made of a material selected from the group consisting of platinum, rhodium, palladium, platinum-rhodium, and platinum-palladium.

7. An oxygen concentration sensing apparatus according to claim 1 or 2, further comprising an electric circuit for making an electric current flow intermittently from said first electrode through said solid electrolyte to said second electrode to maintain constant the concentration of oxygen at the boundary between at least one of said electrodes and said electrolyte.

8. An oxygen concentration sensing apparatus according to claim 1 or 2, wherein said solid electrolyte is made of a material selected from the group consisting of $Y_2O_3$-$ZrO_2$ and $CaO$-$ZrO_2$.

9. An oxygen concentration sensing apparatus according to claim 1 or 2, wherein said nonconductive heat-resistant material layer is made of a material selected from the group consisting of heat-resistant glass, alumina, and zirconia.

* * * * *